United States Patent
Frybarger

(12)
(10) Patent No.: US 6,202,479 B1
(45) Date of Patent: *Mar. 20, 2001

(54) AUDIBLE SOIL MOISTURE MONITORING APPARATUS, SYSTEM AND METHOD

(76) Inventor: Scott Frybarger, 1253 W. Nelson, #1, Chicago, IL (US) 60657

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/310,565

(22) Filed: May 12, 1999

(51) Int. Cl.[7] ............... G01N 5/02; G01F 23/00
(52) U.S. Cl. ............ 73/73; 73/304 C; 324/694; 340/620; 340/604
(58) Field of Search .............. 73/73, 304 C; 200/61.04, 62.05; 340/602, 620, 604; 137/78.3; D10/56; 324/694, 696

(56) References Cited

U.S. PATENT DOCUMENTS

| | | | |
|---|---|---|---|
| D. 143,432 | * | 1/1946 | Lawrence ............... D10/56 |
| D. 245,585 | * | 8/1977 | Bru ........................ D10/56 |
| D. 255,334 | * | 6/1980 | Corbin et al. .......... D10/56 |
| 3,927,370 | | 12/1975 | DeBough . |
| 3,968,428 | | 7/1976 | Numoto . |
| 4,020,417 | | 4/1977 | Brehob et al. . |
| 4,268,824 | | 5/1981 | Phillips . |
| 4,503,707 | | 3/1985 | Rosa et al. . |
| 4,514,722 | | 4/1985 | Batcheler et al. . |
| 4,791,413 | | 12/1988 | Lyczek . |
| 4,796,017 | * | 1/1989 | Merenda .............. 73/304 C |
| 4,931,775 | | 6/1990 | Sheriff . |
| 5,621,669 | * | 4/1997 | Bjornsson ........... 364/571.01 |

* cited by examiner

*Primary Examiner*—Harshad Patel
(74) *Attorney, Agent, or Firm*—Patents +TMS

(57) ABSTRACT

A soil moisture monitoring apparatus, system and method for monitoring the soil moisture content of a given volume of soil in which a plant is growing are provided. The apparatus, system and method allow a plant caretaker to be alerted when the soil moisture content in the soil drops below a pre-determined level. When the soil moisture content drops below a predetermined level, an audible signal may be generated alerting the plant caretaker of the need to add water. The audible signal generated generally corresponds to a recognizable sound that a creature embodied by a creature-shaped housing makes in nature. The creature-shaped housing containing the audible signal generator mechanism may be placed around or attached to the plant such that the audible signal may be readily heard and the creature-shaped housing is visible.

20 Claims, 1 Drawing Sheet

AUDIBLE SOIL MOISTURE MONITORING APPARATUS, SYSTEM AND METHOD

BACKGROUND OF THE INVENTION

The present invention generally relates to an apparatus, a system and a method for monitoring soil moisture. More specifically, the present invention relates to an apparatus, a system and a method for determining the soil moisture content of a volume of soil and alerting a plant caretaker of a need to add water to the soil for the health of a plant that resides within the soil.

Plants, of course, are often used as decorative accessories in the home, at many business and the like. Often, plants may be difficult to maintain. Different plants typically require different watering needs. Often, people who have several plants water all of their plants simultaneously, whether water is required for the plant or not. Likewise, plants often go unwatered and become too dry and may subsequently die.

It is, however, generally known to provide an apparatus to monitor soil moisture content to assist in determining watering needs for a plant. Typically, a monitor is placed within a volume of soil that measures a conductance across probes within the soil. The strength of an electrical current across the probes is dependent on the conductance of the soil, which, in turn, is dependent on the moisture content of the soil. A signal may be produced indicative of the soil moisture content. The signal may be interpreted to determine if the plant in which the probe is placed requires water.

However, known soil moisture monitors are deficient in many aspects. First, known soil moisture monitoring apparatuses are large and unsightly and tend not to fit in the natural settings of a potted plant. Still further, known visual alert systems consist of blinking lights that may become hidden in the pot. Known audible alert systems typically consist of a series of beeps or buzzing sounds. Such visual and audible alert systems may not fit within the natural setting of a household plant.

Therefore, an improved soil moisture monitoring apparatus, system and method are needed that overcome the deficiencies of known systems.

SUMMARY OF THE INVENTION

The present invention provides an apparatus, a system and a method for monitoring soil moisture content and audibly alerting a plant caretaker of the need to add water for the needs of a plant within the soil. More specifically, the present invention provides an apparatus, a system and a method for monitoring soil moisture content wherein the sensing mechanism is small and hidden from view and the audible signal generating mechanism is provided within a housing that is shaped like a creature that may be found around plants or otherwise in nature. Furthermore, the audible signal generated by the monitoring apparatus generally corresponds to the creature embodied in the creature shaped housing.

To this end, in an embodiment of the present invention, a soil moisture monitoring apparatus is provided. The apparatus has a soil moisture sensor. A processor is connected to the soil moisture sensor. An audible signal generator is connected to the processor capable of generating an audible signal. A housing shaped like a known creature is provided in which the creature is capable of producing a recognizable sound. The audible signal generator is associated with the housing, and the audible signal generated by the audible signal generator activates replication of the recognizable sound of the creature.

In an embodiment, the creature-shaped housing is a frog shape.

In an embodiment, the recognizable sound generated by the audible signal generator replicates the sound of a frog.

In an embodiment, the creature-shaped housing is a cricket shape.

In an embodiment, the recognizable sound generated by the audible signal generator replicates the sound of a cricket.

In an embodiment, the creature-shaped housing is a bird shape.

In an embodiment, the recognizable sound generated by the audible signal generator replicates the sound of a bird.

In an embodiment, a power supply means is connected to the processor.

In an embodiment, a switch is associated with the power supply means.

In an embodiment, a look-up table is associated with the processor and provides a reference to the processor indicative of a predetermined soil moisture level.

In an embodiment, an input means is associated with the processor.

In another embodiment of the present invention, a system is provided for monitoring soil moisture. The system has a volume of soil with a soil moisture content. A plant grows within the volume of soil. A soil moisture sensor is located in the volume of soil. A processor is attached to the soil moisture sensor. An audible signal generator is connected to the processor. A housing shaped like a known creature is provided. The audible signal generator is associated with the housing and the audible signal generated by the audible signal generator activates replication of the recognizable sound of the creature.

In an embodiment, a look-up table is associated with the processor. The look-up table provides a reference to the processor indicative of the predetermined soil moisture level.

In an embodiment, a creature-shaped housing contains the audible signal generator therein.

In an embodiment, an input means is associated with the processor.

In another embodiment of the present invention, a method is provided for monitoring soil moisture. The method comprises the steps of: providing a volume of soil having a soil moisture content; providing a plant growing within the volume of soil; providing a soil moisture sensor connected to a processor, the processor connected to an audible signal generator; providing a housing replicating a creature capable of producing a recognizable sound associated with the creature connected to the audible signal generator; placing the soil moisture sensor in the volume of soil; and placing the creature-shaped housing around the plant.

In an embodiment, an input means is connected to the processor and inputs a reference into the processor. The reference corresponds to a predetermined soil moisture level desired for the plant.

In an embodiment, a power supply means is connected to the processor.

In an embodiment, a look-up table associated with the processor is provided.

It is, therefore, an advantage of the present invention to provide a soil moisture monitoring apparatus, system and method that allow a plant caretaker to determine when water should be added to a volume of soil in which a plant is growing.

Another advantage of the present invention is to provide a soil moisture monitoring apparatus, system and method in which the sensing mechanism is small and can be hidden from view within the volume of soil or pot of soil.

Another advantage of the present invention is to provide a soil moisture monitoring apparatus, system and method that has an input means allowing a plant caretaker to adjust a reference that would determine when the plant caretaker should be alerted depending on the watering needs of different plants.

A still further advantage of the present invention is to provide a soil moisture monitoring apparatus, system and method that has a power supply providing an electrical current through the monitor.

Yet another advantage of the present invention is to provide a soil moisture monitoring apparatus, system and method that emits an audible signal alerting a plant caretaker of the need to add water to the plant.

Another advantage of the present invention is to provide a soil moisture monitoring apparatus, system and method wherein an audible signal generally corresponds to a sound that a creature in nature would make.

A still further advantage of the present invention is to provide a soil moisture monitoring apparatus, system and method wherein the audible signal generating device is contained within a creature-shaped housing that would be found within nature.

A still further advantage of the present invention is to provide a soil moisture monitoring apparatus, system and method wherein the audible signal generating mechanism contained within the creature-shaped housing may be placed in and around the plant in a way that may be audibly heard and visually pleasing to the eye.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
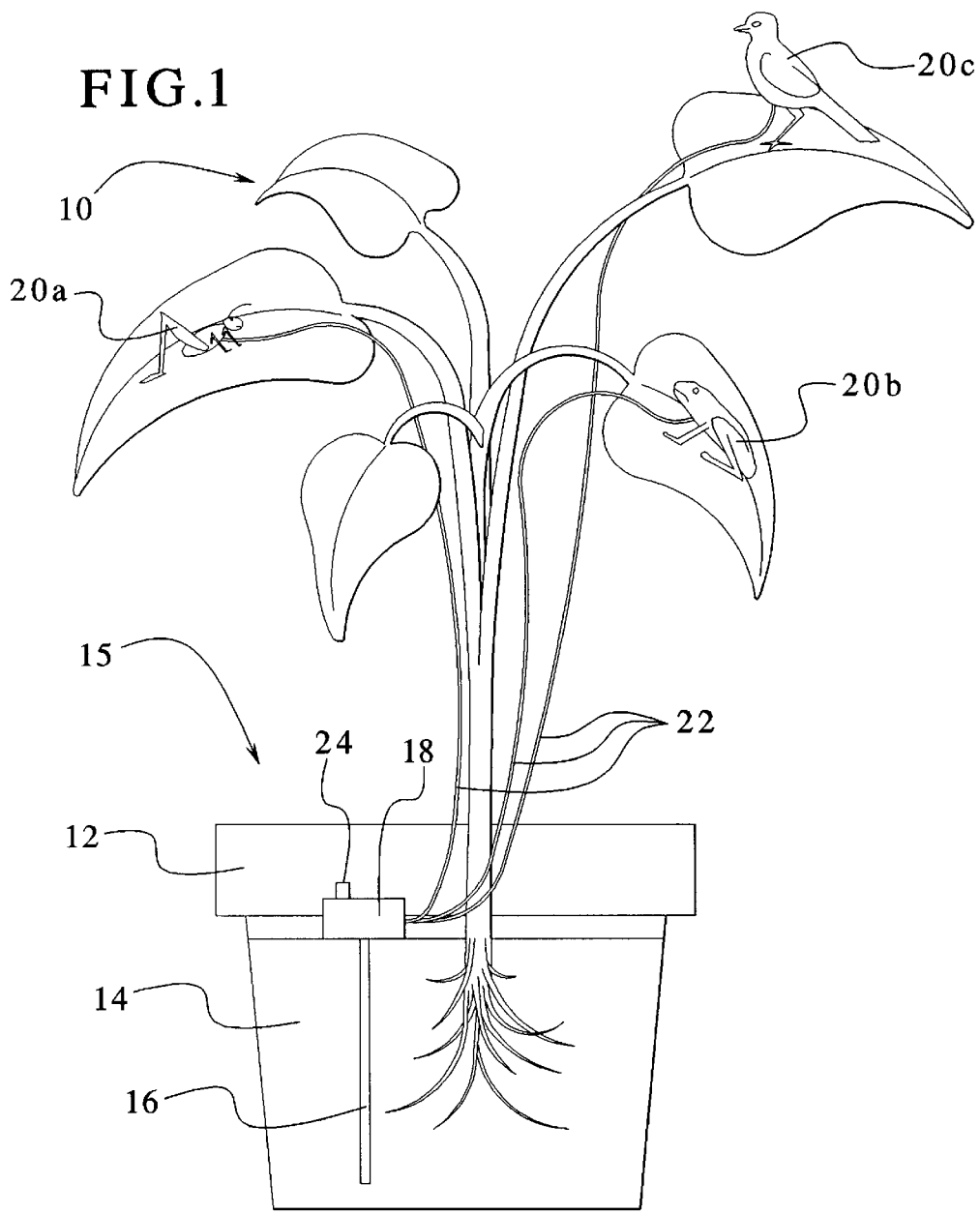
FIG. 1 illustrates a schematic view of an embodiment of the present invention including an audible soil moisture monitor, a plant, and a pot of soil.

Referring now to the drawings wherein like numerals refer to like parts, FIG. 1 generally illustrates a schematic view of an audible soil moisture monitor 15, a plant 10 and a pot 12 filled with soil 14. The plant 10 is illustrated growing within and out of the pot 12 containing a volume of the soil 14. The plant 10, the pot 12 and the volume of soil 14 generally illustrate, for example, a potted houseplant. The plant 10 may be any houseplant or garden plant well-known to one skilled in the art. The pot 12 may be any size and any shape, and the soil 14 may be any volume necessary to support the plant 10.

The audible soil moisture monitor 15 includes a soil moisture sensor 16, a processor 18, a creature-shaped housing 20a, 20b and/or 20c and a connecting wire 22 to connect the processor 18 to the creature-shaped housing 20a, 20b and/or 20c. The soil moisture sensor 16 may be any such sensor well-known to one skilled in the art. In particular, the soil moisture sensor 16 may detect an electrical current indicative of the soil moisture content of the soil 14. Preferably, the soil moisture sensor 16 is attached to a wire (not shown) that is attached to the processor 18, or is adjustable such that the soil moisture sensor 16 may be deposited at varying depths in the soil 14 depending on varying characteristics of the plant 10, such as plant root depth.

For example, the soil moisture sensor 16 may include a pair of probes (not shown) that are deposited within the soil 14. The probes may be set a distance from one another in the soil 14 so that an electric current may run between them through the soil 14. The moisture of the soil 14 affects the conductance and, hence, the signal detected between the probes. A high soil moisture content produces a relatively high conductance, and, therefore, corresponds to a relatively strong electrical current across the probes. A low soil moisture content corresponds to a relatively weak electrical current across the probes. Therefore, the soil moisture sensor 16 may detect an electrical current indicative of the soil moisture content of the soil 14. Of course, other like soil moisture sensors may be utilized for the purposes of generating a soil moisture signal indicative of the soil moisture content of the soil 14. Such sensors are known to those skilled in the art.

Attached to the soil moisture sensor 16 is a processor 18. The processor 18 is capable of interpreting, for example, the strength of the electrical current generated by the soil moisture sensor 16. Attached to the processor 18 may be a power supply 50. The power supply 50 provides the necessary power for the monitor 15. The power supply 50 may supply an electric current to the soil moisture sensor 16. The power supply 50 may be activated by, for example, a switch 24. The switch preferably has "on" and "off" positions to control activation of power.

Figure 2:
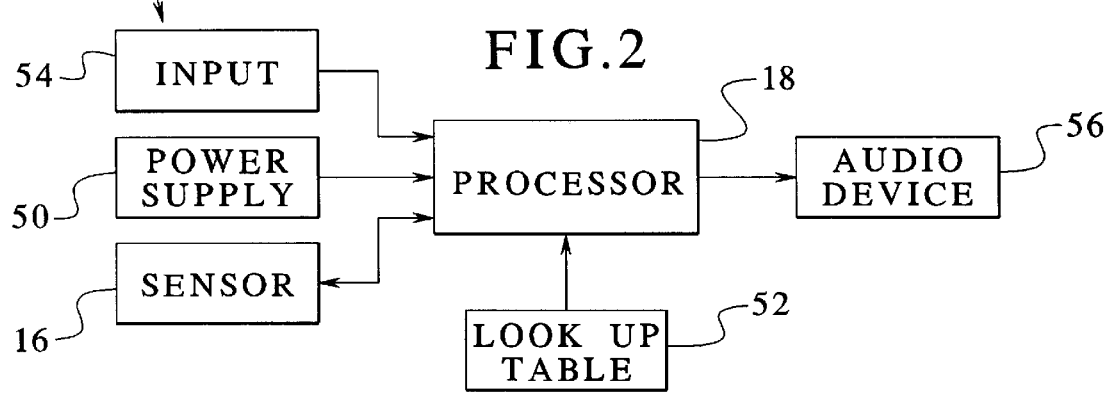
FIG. 2 illustrates a black box diagram of a system of an embodiment of the present invention.

Also attached to the processor 18 may be an input device 54 as shown in FIG. 2. The input device 54 allows a plant caretaker to adjust a reference in the processor 18. For example, the processor 18 may compare the strength of a signal detected by the soil moisture sensor 16 to a reference stored in a look-up table 52 to determine whether the processor 18 should activate a signal, such as an audible signal produced by an audio device 56 in any one or more of the creatures 20a, 20b and/or 20c. The device 56 may receive a signal from the processor 18 to activate an audible signal that may be heard by a plant caretaker. The audio device 56 may include a circuit with a speaker and amplifier attached thereto to generate an audible signal. Other like devices well-known to those skilled in the art may be utilized for this purpose.

The look-up table 52 is particularly necessary to select watering requirements for various types of plants in which the monitor 15 may be implemented. For example, a plant that, in nature, may be found within a tropical rain forest may require a very high soil moisture content. The plant caretaker may, therefore, wish to maintain a high soil moisture content in the soil 14. The caretaker, therefore, sets the look-up table 52 associated with the processor 18 via the input device 54 to alert him when the soil moisture content of the soil 14 drops below the predetermined level to maintain a high soil moisture content in the soil 14. Alternatively, if a cactus, for example, is being maintained that typically requires very little water as the plant 10 in the soil 14, the plant caretaker may set the look-up table 52 associated with the processor 18 via the input device 54 to alert him when the soil moisture content drops below a very low level corresponding to a very dry moisture content of the soil 14.

The audio device 56 is preferably contained within and associated with each one of the creature-shaped housings 20*a*, 20*b* and/or 20*c*. The creature-shaped housings 20*a*, 20*b* and/or 20*c* may appear like creatures that may be found in and around plants or otherwise in nature. Further, the sound generated by the audio device 56 may be a sound that a creature embodied in the creature-shaped housing 20*a*, 20*b* and/or 20*c* may make. For example, the creature-shaped housing 20*a* may be a cricket wherein the audio device 56 generates an audible signal corresponding to the sound a cricket makes: a "chirrup." Further, the creature-shaped housing 20*b* may be in the shape of a frog wherein the audible signal generated by the audio device may be a sound corresponding to the sound a frog makes: a "ribbit." Additionally, the creature-shaped housing 20*c* may appear in the shape of a bird wherein the audible signal generated by the audio device may be a sound corresponding to the sound a bird makes: a "tweet." Other like creatures may, of course, be implemented, and the invention should not be construed as limited to the specific creature-shaped housings 20*a*, 20*b* and/or 20*c*.

The creature-shaped housings 20*a*, 20*b* and/or 20*c* containing the audio device 56 may be connected to the processor 18 via the wire 22. The wire 22 provides an electrical connection between the processor 18 and the audio device 56 contained within the creature-shaped housings 20*a*, 20*b* and/or 20*c*.

Preferably, a single creature-shaped housing 20*a*, 20*b* or 20*c* may be connected to the processor 18 via the wire 22; in FIG. 1, however, three creature-shaped housings 20*a*, 20*b* and 20*c* are shown connected to the processor 18. However, any number of creature-shaped housings may be connected to a single processor without departing from the spirit and scope of the present invention.

FIG. 2 illustrates a black box diagram of the audible moisture monitor 15. The audible moisture monitor 15 includes the soil moisture sensor 16 with the processor 18 attached thereto. A power supply 50 may be connected to the processor 18 in order to supply an electrical current to the monitor 15. The power supply 50 may have a switch. When the switch is in the "on" position, the power supply 50 activates the monitor 15 such that the sensor 16 is capable of detecting moisture in the soil 14, the processor 18 may interpret the signal produced by the sensor 16, and the audio device 56 may produce a sound in one or more of the creature-shaped housings 20*a*, 20*b* and/or 20*c*.

The input device 54 is attached to the processor 18 allowing a plant caretaker to specify a particular soil moisture content that maintains a houseplant in a preferred watered state. The input device 54 may be adjustable in accordance with the soil moisture needs of the houseplant that is planted within the soil 14. The look-up table 52 may be provided and associated with the processor 18 to store various watering needs for specific types of plants. The input device 54 may be used to alter the values stored in the look-up table 52. The audio device 56 is preferably attached to the processor 18. The audio device 56 may cause an audible signal to emit from the audio device 56. The audio device 56 preferably emits an audible signal that corresponds to a sound that a creature in nature makes. The audio device 56 is preferably embodied within a replica of such a creature as shown by the creature-shaped housings 20*a*, 20*b* and/or 20*c* of FIG. 1.

Preferably, the monitor 15 of the present invention includes a single one of the creature-shaped housings 20*a*, 20*b* and/or 20*c* associated with the monitor 15. Therefore, a single one of the creature-shaped housings 20*a*, 20*b* and/or 20*c* may be secured or otherwise placed on the plant 10 for support. Of course, more than one of the creature-shaped housings 20*a*, 20*b* and/or 20*c* may be simultaneously implemented. In addition, each of the audio devices 56 may be independently controlled by the processor 18 to respond to various conditions of the soil 14. Accordingly, the processor 18 may activate one or more of the audio devices 56 associated with the creature-shaped housings 20*a*, 20*b* and/or 20*c* depending on the sensed conditions of the soil 14.

Preferably, the creature-shaped housings 20*a*, 20*b* and/or 20*c* are constructed from a ceramic material. The housings 20*a*, 20*b* and/or 20*c* are, of course, constructed to contain their required audio devices 56 to replicate the sounds typically produced by the creatures that the housing 20*a*, 20*b* and/or 20*c* represent. Of course, other materials may be used, and the present invention should not be construed as being limited to the type of material for the housings 20*a*, 20*b* and/or 20*c*.

It should be understood that various alterations, adjustments, changes and modifications to the presently preferred embodiments described herein will be apparent to those skilled in the art. Such changes and modifications may be made without departing from the spirit and scope of the present invention and without diminishing its attendant advantages. It is, therefore, intended that such alterations, adjustments, changes and modifications be covered by the appended claims.

I claim:

1. A soil moisture monitoring apparatus comprising:
   a soil moisture sensor that detects levels of soil hydration and generates a signal indicative thereof;
   a processor connected to the soil moisture sensor, wherein the processor receives the signal from the sensor;
   an audible signal generator connected to the processor wherein the audible signal generator produces an audible signal; and
   a plurality of housings, each shaped like a known living creature and each connected to the processor, wherein said plurality of housings each include said audible signal generator, wherein the audible signal generated by the audible signal generator independently activates replication of a recognizable sound produced by the known living creature in response to a predetermined level of the soil hydration.

2. The apparatus of claim 1 wherein the creature-shaped housing is a frog shape.

3. The apparatus of claim 1 wherein the recognizable sound generated by the audible signal generator replicates a frog-like sound.

4. The apparatus of claim 1 wherein the creature-shaped housing is a cricket shape.

5. The apparatus of claim 1 wherein the recognizable sound generated by the audible signal generator replicates a cricket-like sound.

6. The apparatus of claim 1 wherein the creature-shaped housing is a bird shape.

7. The apparatus of claim 1 wherein the recognizable sound generated by the audible signal generator replicates a bird-like sound.

8. The apparatus of claim 1 further comprising:
   a power supply connected to the processor.

9. The apparatus of claim 8 further comprising:
   a switch associated with the power supply means.

10. The apparatus of claim 1 further comprising:
    a look-up table associated with the processor wherein the look-up table provides a reference to the processor indicative of a predetermined soil moisture level.

11. The apparatus of claim 1 further comprising:

means for inputting connected to the processor for inputting information.

12. A system for monitoring soil moisture, the system comprising:

a volume of soil having a soil moisture content;

a plant growing within the volume of soil;

a soil moisture sensor within the volume of soil, wherein the sensor measures the soil moisture content and generates a signal indicative thereof;

a processor attached to the soil moisture sensor that receives the signal from the sensor;

audible signal generators connected to the processor; and a plurality of housings, each shaped like a known living creature and each connected to the processor, wherein each of the audible signal generators are located within each of the plurality of housings, and further wherein an audible signal generated by the audible signal generators activate replication of a recognizable sound replicating that of a sound produced by the known creature, and further wherein the audible signal is independently activated in response to a predetermined level of the soil moisture content.

13. The system of claim 12 further comprising:

a look-up table associated with the processor wherein the look-up table provides a reference to the processor indicative of a predetermined soil moisture level.

14. The system of claim 12 further comprising:

a creature-shaped housing having the audible signal generator therein.

15. The system of claim 12 further comprising:

means for inputting connected to the processor for inputting information.

16. A method for monitoring soil moisture, the method comprising the steps of:

providing a volume of soil having a soil moisture content;

providing a plant within the volume of soil;

providing a soil moisture sensor connected to a processor, the soil moisture sensor producing a signal indicative of the soil moisture content and sending the signal to the processor, wherein the processor is connected to an audible signal generator;

providing housings replicating living creatures that independently produce recognizable sounds associated with sounds produced by the living creatures in response to a predetermined level of soil hydration wherein the creatures are connected to the audible generator;

placing the soil moisture sensor in the volume of soil; and placing the housings on the plant.

17. The method of claim 16 further comprising the steps of:

providing an input means connected to the processor; and inputting a reference via the input means into the processor wherein the reference corresponds to a predetermined soil moisture level desired for the plant.

18. The method of claim 16 further comprising the step of:

providing a power supply means connected to the processor.

19. The method of claim 16 further comprising the step of:

providing a look-up table associated with the processor.

20. A system for monitoring soil moisture content for a plant embedded in soil, the system comprising:

a soil moisture sensor in the soil, wherein the soil moisture sensor is independently programmable to sense varying levels of the soil moisture content and produce signals indicative of the soil moisture content; and a plurality of housings shaped like known living creatures, wherein each of the plurality of housings have an audible signal generator that receives the signals from the sensor, wherein each of the audible signal generators produces a sound replicating a sound produced by each one of the known living creatures, wherein the sound is independently activated in response to a predetermined level of the soil moisture content sensed by the sensor.

* * * * *